(12) United States Patent
Lim (10) Patent No.: US 12,016,749 B2
(45) Date of Patent: Jun. 25, 2024

(54) DIGITAL IMPLANT SYSTEM

(71) Applicant: Junghoon Lim, Chungcheongnam-do (KR)

(72) Inventor: Junghoon Lim, Chungcheongnam-do (KR)

( * ) Notice: Subject to any disclaimer, the term of this patent is extended or adjusted under 35 U.S.C. 154(b) by 0 days.

(21) Appl. No.: 18/454,602

(22) Filed: Aug. 23, 2023

(65) Prior Publication Data
US 2024/0138959 A1     May 2, 2024

(30) Foreign Application Priority Data

Nov. 2, 2022   (KR) ........................ 10-2022-0144800

(51) Int. Cl.
*A61C 9/00*        (2006.01)
(52) U.S. Cl.
CPC .................................. *A61C 9/0053* (2013.01)
(58) Field of Classification Search
CPC ..... A61C 9/0053; A61C 9/004; A61C 9/0046; A61C 13/0004
See application file for complete search history.

(56) References Cited

U.S. PATENT DOCUMENTS

| | | | | |
|---|---|---|---|---|
| 2009/0111071 A1* | 4/2009 | Yau | ......................... | A61C 8/005 433/173 |
| 2010/0145898 A1* | 6/2010 | Malfliet | .................. | G06V 20/20 703/1 |
| 2011/0123955 A1* | 5/2011 | Yau | ...................... | A61C 8/0077 433/201.1 |
| 2011/0196524 A1* | 8/2011 | Giasson | .................. | B33Y 50/00 700/118 |

(Continued)

FOREIGN PATENT DOCUMENTS

| | | |
|---|---|---|
| JP | 2018-061636 A | 4/2018 |
| KR | 10-2005-0059134 A | 6/2005 |
| KR | 10-2011-0001278 A | 1/2011 |

(Continued)

OTHER PUBLICATIONS

"Request for the Submission of an Opinion" Office Action issued in KR 10-2022-0144800; mailed by the Korean Intellectual Property Office on Dec. 23, 2022.

(Continued)

*Primary Examiner* — Ralph A Lewis
(74) *Attorney, Agent, or Firm* — Studebaker & Brackett PC (57) ABSTRACT

The present disclosure provides a digital implant system including: detecting an region where a intact first tooth among a plurality of teeth is disposed based on a panorama and a CT device for upper and lower jaws where the plurality of teeth of a user are disposed, and acquiring first oral information of the upper and lower jaws; acquiring first surface information by scanning a user's face through an imaging device; generating an image of a temporary denture based on an auto-bone tooth bone graft material; determining a disposition form of the upper and lower jaws of an implant subassembly; acquiring second oral information on the upper and lower jaws where the implant subassembly is disposed and second surface information by scanning the user's face through the imaging devices; and generating an image of a prosthesis that is coupled to the implant subassembly.

1 Claim, 6 Drawing Sheets

(56) References Cited

U.S. PATENT DOCUMENTS

2011/0276159 A1* 11/2011 Chun ................ A61C 13/0004
700/98

FOREIGN PATENT DOCUMENTS

| KR | 10-1735783 B1 | 5/2017 |
| KR | 10-2019-0025083 A | 3/2019 |
| KR | 10-2020-0072250 A | 6/2020 |

OTHER PUBLICATIONS

"Written Decision on Registration" Office Action issued in KR 10-2022-0144800; mailed by the Korean Intellectual Property Office on Mar. 29, 2023.

* cited by examiner

DIGITAL IMPLANT SYSTEM

CROSS-REFERENCE TO RELATED APPLICATIONS

This application claims benefit of priority to Korean Patent Application No. 10-2022-0144800 filed Nov. 2, 2022, the entire contents of which are incorporated herein by reference.

BACKGROUND

1. Field

The present invention relates to a digital implant system.

2. Description of Related Art

In dental treatment, dental implant treatment is to transplant artificial teeth. Dental implant is a treatment to restore a function of teeth by implanting a fixture made of titanium or a titanium alloy, which does not have a rejection reaction in the human body, into an alveolar bone where teeth have been removed, and then fixing artificial teeth. A denture may damage the surrounding teeth and bones over time. On the other hand, an implant does not damage the surrounding tooth tissue and prevent teeth from decaying while having the same function and shape as natural teeth, and as a result, can be used semi-permanently.

Briefly describing the dental implant treatment, first, a groove corresponding to a dimension of the fixture is formed in the alveolar bone through a drilling and tapping process, and the fixture is implanted into the alveolar bone. When the fixture is fixed to the alveolar bone by bone fusion, a healing abutment is fixedly fastened to the fixture to aesthetically reconstruct a gum. When the gum is aesthetically reconstructed, the healing abutment is removed from the fixture, impression coping is fastened to the fixture, an impression body is covered to obtain impression, and a fixing abutment and a permanent dental prosthesis, that is, a crown are manufactured based on the obtained impression. Meanwhile, while the fixing abutment and the permanent dental prosthesis are manufactured, the healing abutment is again fastened to the fixture. When the fixing abutment and the permanent dental prosthesis are manufactured, the healing abutment is removed from the fixture again, the fixing abutment is fixedly fastened to the fixture, and the permanent dental prosthesis is fixedly coupled on the fixing abutment.

Conventionally, when establishing an implant plan using a dental implant planning program, since the position and angle of the prosthesis such as the fixture, the abutment, and the virtual crown are entirely determined by the experience and feeling of the program user performing the procedure, there is a deviation between users. As a result, there is a problem in that the reliability of the procedure is impaired.

In addition, since a guide for establishing an implant plan was not provided at all, users should repeatedly revise the plan, which soon acted as a factor that increases the time required to establish the implant plan and the complexity of the procedure.

Accordingly, there is a need for a digital implant system that automatically obtains information on an internal structure of an oral cavity to reduce the time required to establish the implant plan and the complexity of the procedure when establishing the implant plan, and establishes an implant plan based on the obtained information.

Meanwhile, unlike natural teeth, in the case of the implant, since an implant subassembly including the fixture and the fixing abutment is coupled with the prosthesis, when sticky food or liquid enters the oral cavity, the coupling relationship between the implant subassembly and the prosthesis may be loosened or released during chewing activities. Accordingly, researches on this are required.

SUMMARY

The present invention provides a digital implant system that obtains information on an internal structure of an oral cavity to reduce a time required to establish an implant plan and complexity of a procedure when establishing the implant plan, establishes the implant plan based on the obtained information, and reduces a case where a coupling relationship between an implant subassembly and a prosthesis is loosened or released during chewing activities.

In an aspect of the present invention, a method for configuring an implant is performed by a digital implant system, which includes a computing device including a storage unit, a communication unit, a control unit, and a user input unit, a panorama device, a computed tomography (CT) device, and a 2D and 3D imaging device.

The method includes operations of: capturing, by the panorama device and the CT device, images of an upper jaw and a lower jaw of a user; detecting, by the control unit of the computing device, a region, in which an intact teeth is located, based on the images captured by the panorama device and the CT device; generating, by the control unit of the computing device, first oral information including information on the upper jaw, the lower jaw, and the first region; acquiring, by the 2D and 3D imaging device, first surface information of a face of the user by scanning the face of the user; generating, by the control unit of the computing device, an image of temporal dentures including a material of an autogenous bone graft, based on the first oral information and the first surface information, wherein the material of the autogenous bone graft is configured to be consisted of the intact teeth; determining, by the control unit of the computing device, an arrangement of an implant subassembly in the upper jaw and the lower jaw based on the first oral information; acquiring, by the panorama device and the CT device, second oral information on the upper jaw and the lower jaw, in which the implant subassembly is disposed; acquiring, by the 2D and 3D imaging device, second surface information by scanning the face of the user who has the upper jaw and the lower jaw, in which the implant subassembly is disposed; generating, by the control unit of the computing device, an image of a prosthesis configured to be coupled with the implant subassembly, based on the second oral information and the second surface information, identifying, by the control unit of the computing device, based on the first surface information, in the face of the user, a first upper region of a skin of the face of the user, wherein the first upper region is positioned opposite to a first region, in which the upper jaw is disposed inside; identifying, by the control unit of the computing device, based on the first surface information, in the face of the user, a first lower region of the skin of the face of the user, wherein the first lower region is positioned opposite to a second region, in which the lower jaw is disposed inside; identifying, by the control unit of the computing device, based on the second surface information, a second upper region of the skin, which is positioned opposite to the first region; identifying, by the control unit of the computing device, based on the second surface information, a second lower region of the skin, which is positioned opposite to the second region; acquiring, by the control unit of the computing device, change information by identifying a height difference between the first upper region and the second upper region, and a height difference between the first lower region and the second lower region; and adjusting, by the control unit of the computing device, the image of the prosthesis based on the change information.

The prosthesis comprises polymethyl methacrylate (PMMA) teeth. The change information includes information identifying a collapsed region where the skin is collapsed toward an oral cavity, in the second upper region and in the second lower region, and a size and a shape of a PMMA tooth is determined, so that an upper region of the PMMA tooth disposed correspondingly to the collapsed region protrudes out of the oral cavity.

The generating the image of the prosthesis includes operations of: simulating, by the control unit of the computing device, coupling of the implant subassembly with the prosthesis; generating an image of the implant subassembly, which includes a first protrusion provided to be rotatable in a downward direction in which a diameter of the implant subassembly disposed on an outer side surface is widened, and also includes a second protrusion disposed under the first protrusion and provided to be rotatable in a downward direction; and generating the image of the prosthesis, which has an inner space coupled to the implant subassembly, wherein the inner space includes a first recessed groove provided to allow the first protrusion to penetrate into the inner space corresponding to the first protrusion, and also includes a second recessed groove provided to allow the second protrusion to penetrate into the inner space corresponding to the second protrusion.

DETAILED DESCRIPTION

Hereinafter, embodiments of the present invention will be described in detail with reference to the accompanying drawings. In the drawings, the same reference numbers or signs refer to components that perform substantially the same function, and the size of each component in the drawings may be exaggerated for clarity and convenience. However, the technical idea and the core configuration and operation of the present invention are not limited only to the configuration or operation described in the following examples. In describing the present invention, when a detailed description of well-known technology relating to the present invention may unnecessarily make unclear the spirit of the present invention, a detailed description thereof will be omitted.

In embodiments of the present invention, terms including ordinal numbers such as first and second are used only for the purpose of distinguishing one component from other components, and singular expressions include plural expressions unless the context clearly indicates otherwise. Also, in embodiments of the present invention, it should be understood that terms such as 'configured', 'include', and 'have' do not preclude the existence or addition possibility of one or more other features or numbers, steps, operations, components, parts, or combinations thereof. In addition, in the embodiment of the invention, a 'module' or a 'unit' performs at least one function or operation, and may be implemented in hardware or software, or a combination of hardware and software, and may be integrated into at least one module and implemented as at least one processor. In addition, in embodiments of the invention, at least one of the plurality of elements refers to not only all of the plurality of elements, but also each one or all combinations thereof excluding the rest of the plurality of elements. An expression "configured (or set) to" used in the present invention may be replaced by an expression "suitable for," "having the capacity to" "designed to," "adapted to," "made to," or "capable of" depending on a situation. The term "~configured (or set) to" may not necessarily mean "specifically designed to" in hardware. Instead, an expression "~an apparatus configured to" may mean that the apparatus "is capable of" together with other apparatuses or components. For example, a "processor configured (or set) to perform A, B, and C" may mean a dedicated processor (for example, embedded processor) for performing the corresponding operations or a generic-purpose processor (for example, a central processing unit (CPU) or an application processor) that may perform the corresponding operations by executing one or more software programs stored in a memory apparatus.

Hereinafter, embodiments of the present invention will be described in detail with reference to the accompanying drawings. This is to explain in detail to the extent that those skilled in the art can easily practice the invention, and thus, it is to be noted that the technical spirit and scope of the present invention are not limited.

Figure 1:
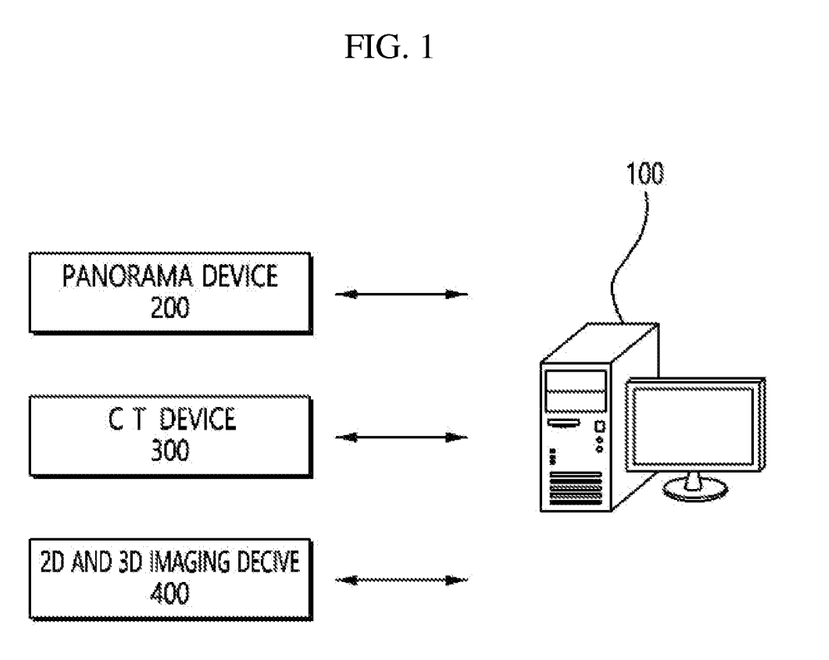
FIG. 1 is a diagram schematically illustrating a digital implant system according to an embodiment of the present invention.
Figure 2:
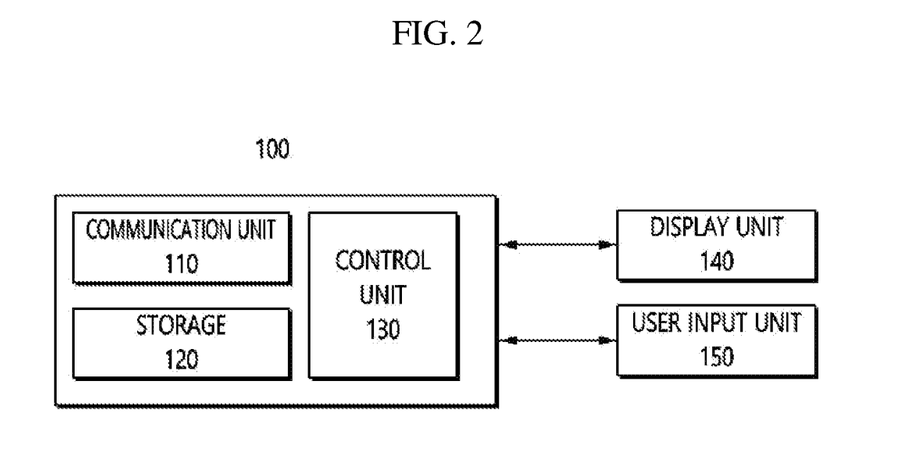
FIG. 2 is a diagram illustrating a configuration of the digital implant system according to the embodiment of the present invention.

FIG. 1 is a diagram schematically illustrating a digital implant system according to an embodiment of the present invention, and FIG. 2 is a diagram illustrating a configuration of the digital implant system according to the embodiment of the present invention.

Referring to FIGS. 1 and 2, a digital implant system according to an embodiment of the present invention includes a computing device 100, a panorama device 200, a CT device 300, and a 2D and 3D imaging device 400.

The computing device 100 according to an embodiment of the present invention is connected to the panorama device 200, the CT device 300, and the 2D and 3D imaging device 400 through a network. In this case, the computing device 100 may transmit and receive digital signals to and from the panorama device 200, the CT device 300, and the 2D and 3D imaging device 400 in a wired or wireless manner.

The computing device 100 according to an embodiment of the present invention includes a display unit 140 displaying imaged images received from the panorama device 200, the CT device 300, and the 2D and 3D imaging device 400 on a screen, a storage unit 120, a communication unit 110, a control unit 130, and a user input unit 150.

The implementation scheme of the display unit 140 is not limited, and the display unit 140 may be implemented in various display schemes such as liquid crystal, plasma, light-emitting diode, an organic light-emitting diode, surface-conduction electron-emitter, carbon nano-tube, and nano-crystal. In the case of the liquid crystal scheme, the display unit 140 includes a liquid crystal display panel, a backlight unit that supplies light to the liquid crystal display panel, a panel driving unit that drives the liquid crystal display panel, and the like. The display unit 140 may be implemented as an OLED panel that is a self-luminous element without a backlight unit.

The user input unit 150 receives various information such as numbers and text information, sets various functions, and receives input signals related to function control of a user terminal, and the user input unit 150 may be configured to include at least one of a keypad and a touchpad that generate an input signal according to a user's touch or manipulation. In this case, the user input unit 150 is configured in the form of a single touch panel (or touch screen) together with a display and may simultaneously perform input and display functions. In addition, the user input unit 150 may use any type of input means that may be developed in the future, in addition to input devices such as a keyboard, a keypad, a mouse, a joystick, and the like.

The storage unit 120 may receive data about imaged images, video, settings for controlling other operations, and the like from the panoramic device 200, the CT device 300, and the 2D and 3D imaging devices 400 connected through the network, and store the data. In addition, the storage unit 120 may store various data according to the processing and control of the control unit 130, which will be described later, and is accessed by the control unit 130 to perform reading, recording, modification, deletion, update, etc., of data. The storage unit 120 may include nonvolatile memories such as a flash-memory, a hard-disc drive, and a solid-state drive (SSD) so that data can be stored regardless of whether or not system power is provided to the computing device 100. In addition, the storage unit 120 may include volatile memories such as a buffer and RAM for temporarily loading data processed by the control unit 130.

The communication unit 110 may communicate with the plurality of computing devices 100 or the plurality of panorama devices 200, the CT device 300, and the 2D and 3D imaging device 400 in a wired or wireless manner, and communicate information such as video, image, text, update files of various control applications, and correction instructions from the panorama device 200, the CT device 300, and the 2D and 3D imaging device 400 in a wired or wireless manner. Therefore, communications can be implemented in various other communication schemes in addition to connection units including a connector or a terminal for wired connection. For example, the communication unit 110 may be configured to perform one or more communications among Wi-Fi, Bluetooth, Zigbee, infrared communication, radio control, ultra-wide band (UWM), wireless USB, and near field communication (NFC). The communication unit 110 may include a communication module such as Bluetooth low energy (BLE), serial port profile (SPP), WiFi direct, infrared communication, Zigbee, and near field communication (NFC). In addition, the communication unit 110 may be implemented in the form of a device, an S/W module, a circuit, a chip, and the like.

The control unit 130 may control an overall operation of components of the computing device 100, the panorama device 200, the CT device 300, and the 2D and 3D imaging device 400 of an oral imaging camera system. The control unit 130 may include control programs (or instructions) for performing the control operation, a nonvolatile memory in which control programs are installed, a volatile memory in which at least a part of the installed control programs is loaded, and at least one processor or a central processing unit (CPU) in which the loaded control programs are executed. In addition, such a control program may also be stored in electronic devices other than the computing device 100.

The control program may include a program(s) implemented in at least one of BIOS, a device driver, an operating system, firmware, a platform, and an application program (application). As an embodiment, the application program may be pre-installed or stored through a server providing the same at the time of manufacturing of the computing device 100, or installed in the computing device 100 by receiving data of the application program received from the outside when used later. The data of the application program may be downloaded from the external server, such as an application market, but is not limited thereto. Meanwhile, the control unit 130 may be implemented in the form of a device, an S/W module, a circuit, and a chip, or a combination thereof.

The panorama device 200 uses radiation for imaging, and images an inside of an oral cavity in a space provided in the device by minimizing movement. The panorama device 200 has a round structure with a sense of perspective inside the oral cavity when imaging a cross section of the oral cavity with the conventional X-rays, and therefore, is an improved device that has limitations in accurately seeing the front, back, left, right, outside and inside of the oral cavity with the naked eye. The panorama device 200 according to an embodiment of the present invention may include all imaging devices that assist dental treatment by imaging the inside of the oral cavity in all directions using radiation.

The CT device 300 refers to a device that may perform computed tomography (CT) imaging by using X-rays and a computer to irradiate a target part of the human body in various directions, collecting the transmitted X-rays with a detector, and reconstructing the difference in absorption of X-rays for that part by a computer using mathematical techniques. The CT device 300 according to an embodiment of the present invention may include all imaging devices that serve to reconstruct the collected information using a computer and display the reconstructed information on the display unit 140.

The 2D and 3D imaging devices operate a plurality of image sensors simultaneously to accurately capture a depth of a subject to be imaged and reproduce a three-dimensional facial image in 2D or 3D, and serve to image distortion-free facial image data. The 2D and 3D imaging devices according to an embodiment of the present invention may include all imaging devices configured to reproduce a three-dimensional facial image using software and a plurality of image sensors in the computing device 100.

Figure 3:
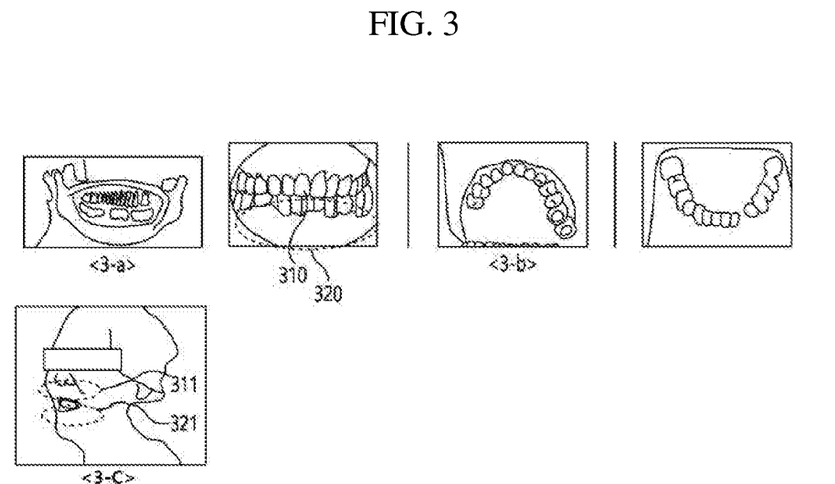
FIG. 3 is diagrams illustrating acquisition of oral information and surface information in the digital implant system according to the embodiment of the present invention.

Referring to FIG. 3, the operation of the digital implant system according to an embodiment of the present invention will be described in more detail.

The panorama device and the CT device may capture images of an upper jaw and a lower jaw of a user.

The control unit 130 of the computing device 100 according to an embodiment of the present invention detects a region, in which an intact teeth is located, based on the images captured by the panorama device and the CT device.

The control unit 130 may generate first oral information including information on the upper jaw, the lower jaw, and the first region.

The 2D and 3D imaging device acquires first surface information of a face of the user by scanning the face of the user.

The control unit 130 may generate an image of temporal dentures including a material of an autogenous bone graft, based on the first oral information and the first surface information. The material of the autogenous bone graft is configured to be consisted of the intact teeth.

The control unit 130 may determine an arrangement of an implant subassembly in the upper jaw and the lower jaw based on the first oral information.

The panorama device and the CT device acquires second oral information on the upper jaw and the lower jaw, in which the implant subassembly is disposed.

The 2D and 3D imaging device acquires second surface information by scanning the face of the user who has the upper jaw and the lower jaw, in which the implant subassembly is disposed.

The control unit 130 may generate an image of a prosthesis configured to be coupled with the implant subassembly, based on the second oral information and the second surface information.

The control unit 130 may identify, based on the first surface information, in the face of the user, a first upper region of a skin of the face of the user. The first upper region is positioned opposite to a first region, in which the upper jaw is disposed inside.

The control unit 130 may identify, based on the first surface information, in the face of the user, a first lower region of the skin of the face of the user. The first lower region is positioned opposite to a second region, in which the lower jaw is disposed inside.

The control unit 130 may identify, based on the second surface information, a second upper region of the skin, which is positioned opposite to the first region.

The control unit 130 may identify, based on the second surface information, a second lower region of the skin, which is positioned opposite to the second region.

The control unit 130 may acquire change information by identifying a height difference between the first upper region and the second upper region, and a height difference between the first lower region and the second lower region.

The control unit 130 may adjust the image of the prosthesis based on the change information.

The prosthesis comprises polymethyl methacrylate (PMMA) teeth.

The change information includes information identifying a collapsed region where the skin is collapsed toward an oral cavity, in the second upper region and in the second lower region, and a size and a shape of a PMMA tooth is determined, so that an upper region of the PMMA tooth disposed correspondingly to the collapsed region protrudes out of the oral cavity.

The control unit 130 may simulate coupling of the implant subassembly with the prosthesis. The control unit 130 may generate an image of the implant subassembly, which includes a first protrusion provided to be rotatable in a downward direction in which a diameter of the implant subassembly disposed on an outer side surface is widened, and also includes a second protrusion disposed under the first protrusion and provided to be rotatable in a downward direction. The control unit 130 may generate the image of the prosthesis, which has an inner space coupled to the implant subassembly. The inner space includes a first recessed groove provided to allow the first protrusion to penetrate into the inner space corresponding to the first protrusion, and also includes a second recessed groove provided to allow the second protrusion to penetrate into the inner space corresponding to the second protrusion. The control unit 130 of the computing device 100 according to an embodiment of the present invention detects a region in which an intact first tooth among the plurality of teeth is disposed based on the panorama and the CT device 300 for the upper and lower jaws where the plurality of teeth of the user are disposed, acquires first oral information of the upper and lower jaws, and scans the user's face through the 2D and 3D imaging device to acquire first surface information. This is because the intact first tooth is extracted in the case of a full jaw implant, not an implant for a partial region and an auto-bone tooth bone graft material may be generated based on the extraction of the intact first tooth.

The control unit 130 may generate an image of the temporary denture based on the first oral information, determine an arrangement of an implant subassembly 520 in the upper jaw and the full jaw based on the first oral information, acquire second oral information on the upper and lower jaws where the implant subassembly 520 is disposed based on the panorama and CT device 300 and second surface information by scanning the user's face through the 2D and 3D imaging device, generate an image of a prosthesis 510 that can be coupled with the implant subassembly 520 based on the acquired second oral information and second surface information.

The control unit 130 may identify, based on the first surface information, a first upper region 311 of a skin existing opposite to a first region 310 in which the upper jaw is disposed and a first lower region 321 of the skin existing opposite to a second region 320 where the lower jaw is disposed among the plurality of regions of the user's face, identify, based on the second surface information, a second upper region of the skin existing opposite to the first region 310 in which the upper jaw is disposed and a second lower region of the skin existing opposite to the second region 320 in which the lower jaw is disposed among the plurality of regions, acquire change information by identifying a height difference between the first upper region 311 and the second upper region and a height difference between the first lower region 321 and the second lower region, and generate the image of the prosthesis 510 based on the change information. Meanwhile, the prosthesis 510 of the digital implant system according to an embodiment of the present invention may include a plurality of PMMA teeth, and the change information may include those identifying a collapsed region 410 that is collapsed into the oral cavity for the second upper region and the second lower region, and determining the size and shape so that the upper region of the first PMMA tooth 411 disposed corresponding to the identified collapsed region 410 among the plurality of PMMA teeth protrudes out of the oral cavity.

FIG. 3 is diagrams illustrating acquisition of oral information and surface information in the digital implant system according to the embodiment of the present invention. <3-a>, <3-b> and <3-c> of FIG. 3 illustrate images obtained with the oral information and the surface information for the upper and lower jaws based on the panorama device 200, the CT device 300, and the 2D and 3D imaging device 400 in the digital implant system according to an embodiment of the present invention, in which the oral information includes information on the first region 310 of the upper jaw and the second region 320 of the lower jaw existing in the oral cavity, and the surface information includes the first upper region 311 of the skin existing opposite to the first region 310 of the upper jaw and the first lower region 321 of the skin existing opposite to the second region 320 of the lower jaw. As such, the digital implant system according to an embodiment of the present invention may use the panorama device 200, the CT device 300, the 2D and 3D imaging device 400, and the computing device 100 connected thereto to obtain the oral information and the surface information.

Figure 4:
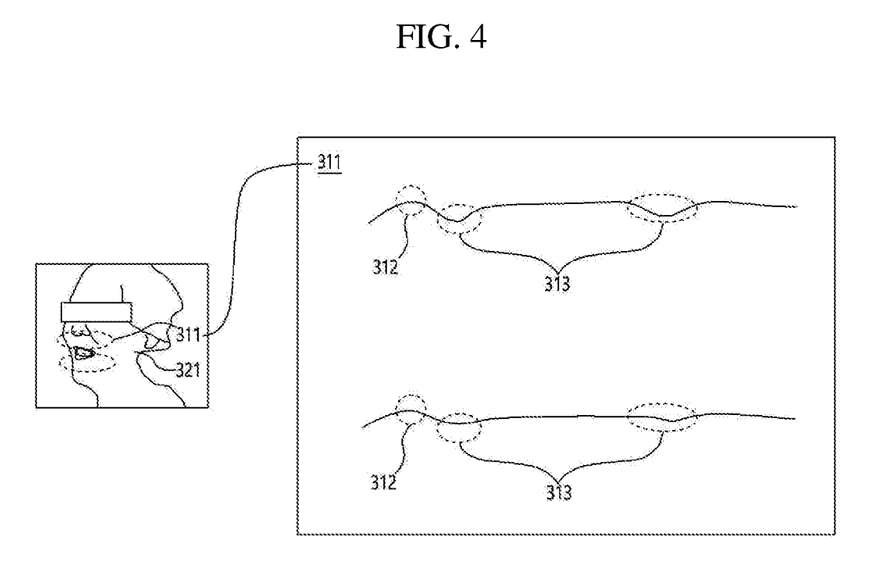
FIG. 4 is a diagram illustrating an operation of identifying a collapsed region from the surface information in the digital implant system according to the embodiment of the present invention.

FIG. 4 is a diagram illustrating an operation of identifying the collapsed region 410 from the surface information in the digital implant system according to the embodiment of the present invention. Referring to FIG. 4, when the arrangement of the implant subassembly 520 in the upper and lower jaws is determined in the oral cavity, it goes through the process of being disposed in the oral cavity based on the arrangement. In this way, when the implant subassembly 520 is disposed inside the oral cavity, the control unit 130 may identify a difference in height of a skin before and after the implant subassembly is disposed based on the first surface information and the second surface information, which are the surface information before and after the implant subassembly 520 is disposed. This is because the skin surrounding the inside of the oral cavity of the user provided with the implant may have depressions, indentations and protrusions, an image of a PMMA tooth may be generated in which each of the depressions, indentations and protrusions may be kept flat with the surrounding skin for aesthetics, and the PMMA teeth reflecting the surface information may be coupled with the implant subassembly 520 so that the skin remains flatter than before the implant procedure. The upper drawing on the left side of FIG. 4 illustrates an image in which a protrusion 312 and an indentation 313 are identified, respectively, in the first upper region 311, and the lower drawing illustrates, as an image, an example in which the PMMA tooth, on which the surface information is reflected, is coupled to the implant subassembly 520 so that the protruding portion 312 and the indentation 313 are flatter than before.

Figure 5:
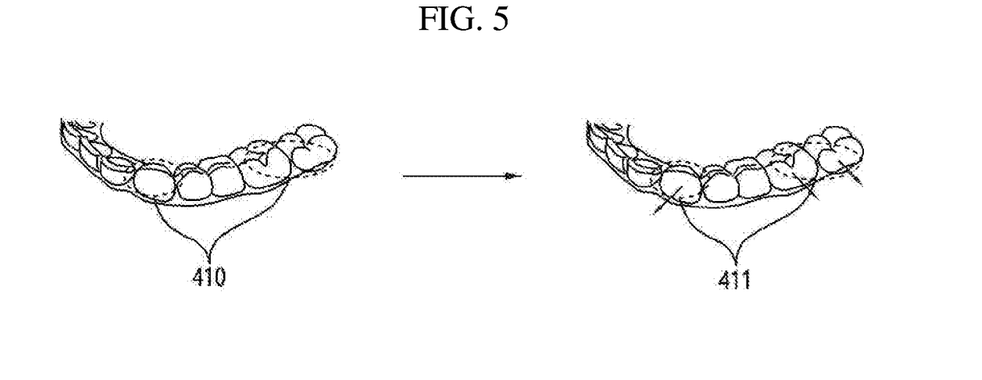
FIG. 5 is a diagram illustrating determining a size and shape of a PMMA tooth in the digital implant system according to the embodiment of the present invention.

FIG. 5 is a diagram illustrating determining a size and shape of a PMMA tooth in the digital implant system according to the embodiment of the present invention.

The control unit 130 of the computing device 100 according to an embodiment of the present invention may determine the size and shape based on the surface information so that a part of the upper region of the PMMA tooth corresponding to the protrusion is collapsed into the oral cavity and determine the size and shape so that a part of the upper region of the first PMMA tooth 411 disposed to correspond to the collapsed region 410 protrudes out of the oral cavity, thereby providing the digital implant system with improved skin aesthetics.

Figure 6:
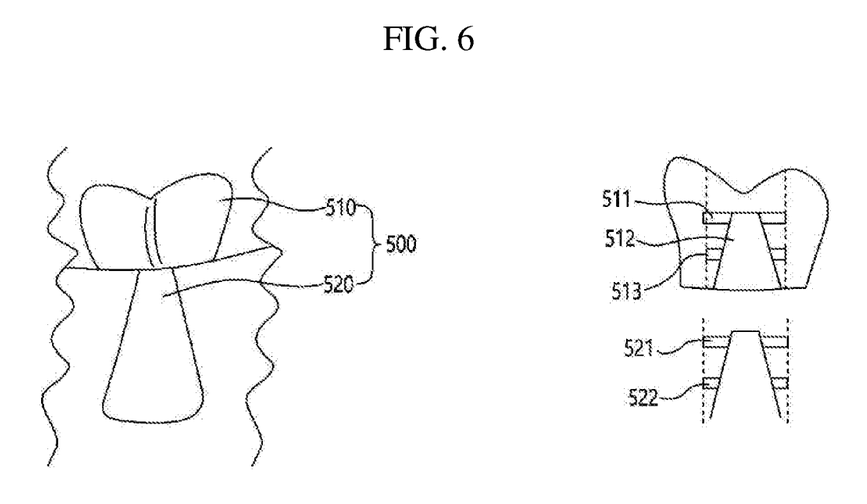
FIG. 6 is a diagram illustrating a configuration of a prosthesis of the digital implant system according to the embodiment of the present invention.

FIG. 6 is a diagram illustrating a configuration of the prosthesis 510 of the digital implant system according to the embodiment of the present invention.

The digital implant system according to an embodiment of the present invention includes a step of coupling the implant subassembly 520 with the prosthesis 510, in which the implant subassembly 520 may include a first protrusion 521 provided to be rotatable in a downward direction in which the diameter of the implant subassemblies 520 respectively disposed on the outer side surface is widened and a second protrusion disposed under the first protrusion 521 and provided to be rotatable in a downward direction, and the prosthesis 510 has an inner space 511 coupled to the implant subassembly 520, and a first recessed groove 512 provided to allow the first protrusion 521 to penetrate into the inner space 511 corresponding to the first protrusion 521 and a second recessed groove 513 provided to allow the second protrusion 522 to penetrate into the inner space 511 corresponding to the second protrusion 522.

Describing in more detail with reference to FIG. 6, the implant subassembly 520 is disposed inside the oral cavity to allow the prosthesis 510 of the full jaw implant to be coupled, and the prosthesis 510 may be floated on the implant subassembly 520 and coupled using an internal filler or the like. In this case, the prosthesis 510 of the conventional implant system is configured to simply adhere through a filling material, and thus, when chewing sticky food, there is a problem in that their coupling may be released. By including the protrusion provided to be rotatable in the downward direction in the implant subassembly 520, when the prosthesis 510 is inserted, it moves downward to facilitate entry, and after the prosthesis 510 is entered, it may be rotated upward to penetrate into the recessed groove in the prosthesis 510 so that they are more strongly coupled.

According to the present invention, it is possible to provide a digital implant system that obtains information on an internal structure of an oral cavity to reduce a time required to establish an implant plan and complexity of a procedure when establishing the implant plan, establishes the implant plan based on the obtained information, and reduces a case where a coupling relationship between an implant subassembly and a prosthesis is loosened or released during chewing activities.

What is claimed is:

1. A method for configuring an implant, performed by a digital implant system, which includes a computing device including a storage unit, a communication unit, a control unit, and a user input unit, a panorama device, a computed tomography (CT) device, and a 2D and 3D imaging device, the method comprising:
    capturing, by the panorama device and the CT device, images of an upper jaw and a lower jaw of a user;
    detecting, by the control unit of the computing device, a region, in which an intact teeth is located, based on the images captured by the panorama device and the CT device;
    generating, by the control unit of the computing device, first oral information including information on the upper jaw, the lower jaw, and the first region;
    acquiring, by the 2D and 3D imaging device, first surface information of a face of the user by scanning the face of the user;
    generating, by the control unit of the computing device, an image of temporal dentures including a material of an autogenous bone graft, based on the first oral information and the first surface information, wherein the material of the autogenous bone graft is configured to be consisted of the intact teeth;
    determining, by the control unit of the computing device, an arrangement of an implant subassembly in the upper jaw and the lower jaw based on the first oral information;
    acquiring, by the panorama device and the CT device, second oral information on the upper jaw and the lower jaw, in which the implant subassembly is disposed;
    acquiring, by the 2D and 3D imaging device, second surface information by scanning the face of the user who has the upper jaw and the lower jaw, in which the implant subassembly is disposed;
    generating, by the control unit of the computing device, an image of a prosthesis configured to be coupled with the implant subassembly, based on the second oral information and the second surface information,
    identifying, by the control unit of the computing device, based on the first surface information, in the face of the user, a first upper region of a skin of the face of the user, wherein the first upper region is positioned opposite to a first region, in which the upper jaw is disposed inside;

identifying, by the control unit of the computing device, based on the first surface information, in the face of the user, a first lower region of the skin of the face of the user, wherein the first lower region is positioned opposite to a second region, in which the lower jaw is disposed inside;

identifying, by the control unit of the computing device, based on the second surface information, a second upper region of the skin, which is positioned opposite to the first region;

identifying, by the control unit of the computing device, based on the second surface information, a second lower region of the skin, which is positioned opposite to the second region;

acquiring, by the control unit of the computing device, change information by identifying a height difference between the first upper region and the second upper region, and a height difference between the first lower region and the second lower region; and adjusting, by the control unit of the computing device, the image of the prosthesis based on the change information, wherein the prosthesis comprises polymethyl methacrylate (PMMA) teeth, and wherein the change information includes information identifying a collapsed region where the skin is collapsed toward an oral cavity, in the second upper region and in the second lower region, and a size and a shape of a PMMA tooth is determined, so that an upper region of the PMMA tooth disposed correspondingly to the collapsed region protrudes out of the oral cavity, and wherein the generating the image of the prosthesis comprises:

simulating, by the control unit of the computing device, coupling of the implant subassembly with the prosthesis;

generating an image of the implant subassembly, which includes a first protrusion provided to be rotatable in a downward direction in which a diameter of the implant subassembly disposed on an outer side surface is widened, and also includes a second protrusion disposed under the first protrusion and provided to be rotatable in a downward direction; and generating the image of the prosthesis, which has an inner space coupled to the implant subassembly, wherein the inner space includes a first recessed groove provided to allow the first protrusion to penetrate into the inner space corresponding to the first protrusion, and also includes a second recessed groove provided to allow the second protrusion to penetrate into the inner space corresponding to the second protrusion.

* * * * *